United States Patent [19]

Lacefield

[11] 4,318,911

[45] Mar. 9, 1982

[54] 5,6-DIARYL-1,2,4-TRIAZINES AS TOPICAL ANTITHROMBOTIC AGENTS

[75] Inventor: William B. Lacefield, Indianapolis, Ind.

[73] Assignee: Eli Lilly and Company, Indianapolis, Ind.

[21] Appl. No.: 220,350

[22] Filed: Dec. 29, 1980

[51] Int. Cl.$^3$ .............................................. A61K 31/53
[52] U.S. Cl. .................................................... 424/249
[58] Field of Search ....................................... 424/249

[56] References Cited

U.S. PATENT DOCUMENTS 3,948,894  4/1976  Lacefield .
3,979,516  9/1976  Lacefield .
3,989,831  11/1976  Lacefield .
4,008,232  2/1977  Lacefield .
4,190,725  2/1980  Lacefield .

OTHER PUBLICATIONS

Abstracts of Papers No. 059, ACS/CSJ Chemical Congress, Honolulu, HI., Apr. 1–6, 1979.
Journal of the Reticuloendothelial Society, vol. 22, No. 4, Oct. 1977, G. P. Lewis.

*Primary Examiner*—Stanley J. Friedman
*Attorney, Agent, or Firm*—James L. Rowe; Arthur R. Whale

[57] ABSTRACT

3-Substituted-5,6-diaryl-1,2,4-triazines active as antithrombotic agents when administered topically.

6 Claims, No Drawings

5,6-DIARYL-1,2,4-TRIAZINES AS TOPICAL ANTITHROMBOTIC AGENTS

BACKGROUND OF THE INVENTION 5,6-Diaryl-1,2,4-triazines are known as anti-inflammatory and antithrombotic agents. Such triazines can be represented by the following structural formula.

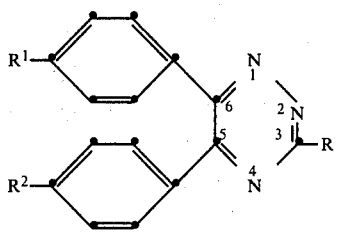

For example, U.S. Pat. No. 3,948,894 discloses a group of 5,6-diaryl-1,2,4-triazines according to formula I in which R is amino, such as dialkylamino, 4-(2-hydroxyethyl)piperazino, 4-hydroxypiperidino, piperidino, α-pipecolino, pyrrolidino, alkylamino, 2-hydroxyethylamino or bis(2-hydroxyethyl)amino and $R^1$ and $R^2$ are, independently, alkoxy, dimethylamino, F or methylsulfinyl. The compounds are said to be anti-inflammatory agents. A divisional application covering compounds in which R is morpholino issued as U.S. Pat. No. 4,008,232, and an earlier divisional application covering a method of treating inflammation with the same group of compounds issued as U.S. Pat. No. 3,979,516. In U.S. Pat. No. 3,989,831, the corresponding 3-chloro derivatives (R is Cl) are claimed as is a method of treating inflammation topically. Topical pharmaceutical formulations useful in the treatment method are also claimed in U.S. Pat. No. 3,989,831.

5,6-Diaryl-1,2,4-triazines in which R is $XR^3$, X is O, S or a direct bond and $R^3$ is alkyl or aralkyl, cycloalkyl or cycloalkylalkyl and $R^1$ and $R^2$ are independently halo, alkyl, alkoxy or dialkylamino are claimed in U.S. Pat. No. 4,013,654. These compounds are stated to be topically-active anti-inflammatory agents. This therapeutic use is claimed separately in U.S. Pat. Nos. 4,018,923 and 4,021,553. Ho and coworkers delineated the anti-inflammatory activity of the 5,6-diaryl-1,2,4-triazines and their high degree of effectiveness as inhibitors of fatty acid cyclooxygenase (50-100 times indomethacin) in a paper presented at the spring 1979 meeting of The American Chemical Society, Medicinal Chemistry Section, Abstract 059.

Some anti-inflammatory agents are known to have antithrombotic activity—see J. B. Smith, page 229 et seq of *Prostaglandin Synthetase Inhibitors*—Editors, H. J. Robinson and J. R. Vane (Raven Press, N.Y. 1974). Applicant knows of no instance where an antithrombotic effect was achieved by topical application of the drug.

In approaching the medical problems involved, in the prevention of thrombosis and particularly in studying the effect of inhibiting platelet aggregation in thrombus formation, some background information might be useful.

A thrombus generally is defined as a plug or clot in a blood vessel or in one of the cavities of the heart, with said plug or clot remaining at the point of formation. When a thrombus is either free-floating in the blood stream or has been removed by the blood stream to a new location, it is referred to as an embolus. These two entities are responsible for a variety of disorders which are generally termed thromboembolic diseases. Such diseases include phlebothrombosis, thrombophlebitis, pulmonary embolism, retinal thrombosis, myocardial infarction, and cerebral infarction.

The chemoprophylactic or chemotherapeutic management of thromboembolic diseases generally involves compounds which fall into one of three categories: (1) platelet aggregation inhibitors, (2) anticoagulants, and (3) fibrinolytic agents. The chemotherapeutic use of fibrinolytic agents is based upon the fact that fibrin frequently forms the primary structural support of a clot. Dissolution of the fibrin should result in lysis of the clot with restoration of blood flow. Thus, thrombi in place can be treated. Anti-coagulants and platelet aggregation inhibitors, on the other hand, generally are employed prophylactically. Anticoagulants are more effective in the treatment of venous thrombosis than arterial thrombosis because of slower blood flow on the venous side which permits coagulation factors, not platelets, to play an important role. While anti-coagulants might not prevent the formation of a platelet-dominated thrombus in the arterial circulation, they can inhibit the stabilization and extension of that thrombosis. However, the successful prophylaxis of arterial thrombosis must deal with the etiologic role of the platelet. The value of platelet function inhibitors in venous thrombosis will be reflected by the extent to which platelets are involved in the formation of those thrombi. Certainly, within the circulatory system, there are regions of stasis in which fibrin formation would be virtually the sole participant in thrombosis, but there would be other regions of high hemodynamic activity where the platelet nidus alone could block the vessel. Between these two extremes, there are situations in which fibrin formation and platelet aggregation occur more or less simultaneously, each supporting the other.

It is an object of this invention to provide platelet aggregation inhibitors which manifest an anti-thrombotic effect when administered topically.

SUMMARY OF THE INVENTION

In fulfillment of the above and other objects, this invention provides a method of achieving an anti-thrombotic effect in mammals by administering an anti-thrombotic drug topically. Those drugs which can be applied topically to achieve anti-thrombotic blood levels are triazines represented by the formula:

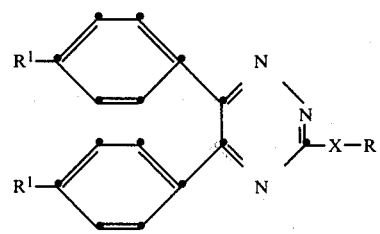

wherein R is $C_1$–$C_4$ alkyl, X is S, O or a direct bond, and each $R^1$ individually is $(C_1$–$C_4)$alkyl-O-, or dimethylamino.

In the above formula, when R is $C_1$–$C_4$ alkyl, the groups represented include methyl, ethyl, n-propyl, isopropyl, sec.-butyl, isobutyl, n-butyl or the like.

Illustrative of compounds coming within the scope of the above formula are illustrated below.

3-ethyl-5,6-bis(4-ethoxyphenyl)-1,2,4-triazine,
3-methylthio-5,6-bis(4-isopropoxyphenyl)-1,2,4-triazine,
3-n-butyloxy-5,6-bis(4-methoxyphenyl-1,2,4-triazine,
5,6-bis(4-ethoxyphenyl)-3-methyl-1,2,4-triazine,
5,6-bis(4-methoxyphenyl)-3-methoxy-1,2,4-triazine,
5,6-bis(4-n-propoxyphenyl)-3-methylthio-1,2,4-triazine,
5,6-bis(4-n-propoxyphenyl)-3-methylthio-1,2,4-triazine,
5,6-bis(4-methoxyphenyl)-3-ethyl-1,2,4-triazine,
3-methyl-5,6-bis(4-methoxyphenyl)-1,2,4-triazine,
3-methoxy-5,6-bis(4-isopropoxyphenyl)-1,2,4-triazine,
5,6-bis(4-methoxyphenyl)-3-methylthio-1,2,4-triazine,
5-(4-ethoxyphenyl)-6-(4-propoxyphenyl)-3-methyl-1,2,4-triazine,
5,6-bis(4-diethylaminophenyl)-3-ethyl-1,2,4-triazine,
5-(4-methoxyphenyl)-6-(4-ethoxyphenyl)-3-methylthio-1,2,4-triazine,
6-(4-dimethylaminophenyl)-3-ethyl-5-(4-methoxyphenyl)-1,2,4-triazine,
5,6-bis(4-dimethylaminophenyl)-3-ethoxy-1,2,4-triazine,
and the like.

The free bases of this invention according to Formula II above are customarily utilized therapeutically in the form of an acid addition salt formed with a non-toxic acid. Useful non-toxic acids for this purpose include inorganic acids such as: hydrochloric acid, nitric acid, phosphoric acid, sulfuric acid, hydrobromic acid, hydriodic acid, phosphorus acid and the like, as well as salts of non-toxic organic acids including aliphatic mono and dicarboxylates, phenyl-substituted alkanoates, hydroxy alkanoates and alkandioates, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogen-phosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

Compounds represented by the above formula, as well as starting materials and intermediates, useful in their preparation are synthesized by known methods. The preparation of 5,6-diaryl-1,2,4-triazines is described generally by J. G. Erickson in Chapter II, pp. 44–84 of "The 1,2,3- and 1,2,4-Triazines, Tetrazines and Pentazines," The Chemistry of Heterocyclic Compounds, Vol. 10, (Interscience Publishers, Inc., New York, N.Y., 1956).

The specific procedure employed to prepare a given 3-substituted-5,6-diaryl-1,2,4-triazine in part is dependent upon the substituent in the 3-position. For example, 3-alkyl-5,6-diaryl-1,2,4-triazines can be prepared directly by the cyclization of acylhydrazones of α-diketones by ammonium acetate in hot acetic acid under controlled conditions; see, e.g., C. M. Atkinson and H. D. Cossey, *J. Chem. Soc.*, 1962, 1805 [*Chem. Abstr.*, 57:4662i (1962)]. The procedure of Neunhoffer and Wwischdol, Ann. 749, 16 (1971) involving the reaction of an alkylamidine, hydrazine and a benzil can also be adapted for the preparation of those compounds of this invention in which R is alkyl X is a direct bond. Such triazines also can be prepared from 3-chloro-5,6-diaryl-1,2,4-triazines by the procedure of E. C. Taylor and S. F. Martin [*J. Amer. Chem. Soc.*, 94, 2874 (1972)] which involves the nucleophilic displacement of chlorine by a Wittig reagent which may be generated in situ from an alkyl-, aralkyl-, or cycloalkyl-triarylphosphonium halide.

3-Chloro-5,6-diaryl-1,2,4-triazines also can be employed to prepare the 3-alkoxy and 3-alkylthio-, 5,6-diaryl-1,2,4-triazines via the nucleophilic displacement of chlorine by the appropriate alcohol or thiol. The 3-alkylthio- compounds can be converted to the 3-alkoxy-, 5,6-diaryl-1,2,4-triazines again via nucleophilic displacement by the appropriate alcohol. The 3-alkylthio-triazines in many cases can be prepared by treating the appropriate 3-mercapto-5,6-diaryl-1,2,4-triazine with the appropriate. 3-mercapto-5,6-diaryl-1,2,4-triazine with the appropriate alkyl halide in the presence of base, particularly when the hydrocarbyl halide is primary or secondary.

3-Chloro-5,6-diaryl-1,2,4-triazines are readily obtained by treating the appropriate 3-hydroxytriazine with phosphorus oxychloride. 3-Hydroxy- and 3-mercapto-5,6-diaryl-1,2,4-triazines in turn can be prepared by condensing the appropriate benzil with semicarbazide or thiosemicarbazide, respectively.

The required benzils are prepared by the oxidation of the corresponding benzoins with copper sulfate in pyridine; see H. T. Clarke and E. E. Driger, *Org. Synthesis, Coll.* Vol. I, 87 (1941). The benzoins in turn are prepared by the condensation of aromatic aldehydes in the presence of cyanide ion; see W. S. Ide and J. S. Buck, *Org. Reactions*, 4, 269 (1948).

Another approach to the synthesis of the compounds of the present invention involves the use of benzils having substituents which can be displaced to give the desired $R^1$ substituent. For example, the halogen on the phenyl ring at the 5-position in a 5-(4-halophenyl)-6-aryl-1,2,4-triazine can be displaced with an alcohol or a dialkylamine to give respectively the corresponding 5-(4-alkoxyphenyl)- or 5-(4-dialkylaminophenyl)- compounds.

The use of two different aromatic aldehydes in the benzoin synthesis leads to unsymmetrical benzils; i.e. a benzil of the formula,

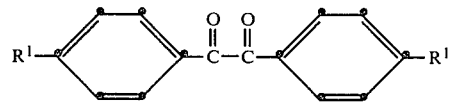

wherein each $R^1$ represents a different group. The use of an unsymmetrical benzil in the above synthetic procedure results in the preparation of a mixture of triazine isomers. For example, the condensation of 4-ethoxy-4'-methoxybenzil with thiosemicarbazide gives a mixture of 5-(4-ethoxyphenyl)-6-(4-methoxyphenyl)-1,2,4-triazine-3-thiol and 6-(4-ethoxyphenyl)-5-(4-methoxyphenyl)-1,2,4-triazine-3-thiol.

It will be recognized by those skilled in the art that such mixtures of triazine isomers are separable by known methods, such as fractional crystallization and chromatography. The isomer separation may be effective upon intermediate mixtures or delayed until the final product stage.

Compounds coming within the scope of Formula II above, among other compounds, are disclosed in my U.S. Pat. No. 4,013,654. The preparation of representative compounds follows:

EXAMPLE 1
Preparation of 5,6-Bis(4-methoxyphenyl)-3-methyl-1,2,4-triazine A reaction mixture was prepared containing 1.2 kg. of anisoin, 3 kg. of cupric sulfate pentahydrate, 4.9 l. of pyridine and 1.2 l. of water. The mixture was heated with stirring overnight at a temperature of about 85° C. The resulting green suspension was poured over 20 kg. of ice and the mixture stirred until the ice had dissolved. Anisil, formed in the above reaction was collected by filtration. The filter cake was washed thoroughly with water to remove all traces of copper sulfate. Yield of anisil was 1167 g. melting at 125°–127° C.

A reaction mixture was prepared from 700 g. of acetamidine hydrochloride, 3 l. of methanol and 241 g. of hydrazine hydrate. The mixture was stirred at ambient temperature under nitrogen for about five minutes at which time a pink color developed. 1.5 kg. of Anisil in 10 l. of methylenedichloride was added followed by 843 g. of triethylamine. The above mixture was stirred overnight under a nitrogen atmosphere. The reaction mixture was extracted successively with water, 2 N aqueous hydrochloric acid, water, 2 N aqueous sodium hydroxide and water. The organic layer was dried, and the dried solution concentrated to about one-third of its original volume. n-Hexane was added to the point of incipient precipitation. A yellow solid comprising 3-methyl-5,6-bis(4-methoxyphenyl)-1,2,4-triazine was collected by filtration. Recrystallization of the filter cake from isopropanol yielded 1400 g. of the triazine melting at 114°–116° C. The compound showed a single spot on tlc.

The preparation of the following compounds coming within the scope of formula II above can be found in U.S. Pat. 4,190,725: 3-ethyl-5,6-bis(4-methoxyphenyl)-1,2,4-triazine; 3-ethylthio-5,6-bis(4-methoxyphenyl)-1,2,4-triazine; 3-isopropylthio-5,6-bis(4-methoxyphenyl)-1,2,4-triazine; 3-methoxy-5,6-bis-(4-methoxyphenyl)-1,2,4-triazine, and 3-ethoxy-5,6-bis-(4-methoxyphenyl)-1,2,4-triazine. Other compounds of particular interest preparable by one or more of the above procedures include 3-methyl-5,6-bis(4-ethoxyphenyl)-1,2,4-triazine, m.p.=104°–106° C.; 3-isopropyl-5,6-bis(4-methoxyphenyl)-1,2,4-triazine, m.p.=87°–89° C.; 3-n-propyl-5,6-(4-methoxyphenyl)-1,2,4-triazine, m.p.=74°–78° C.; 3-ethoxy-5,6-bis(4-methoxyphenyl)-1,2,4-triazine, m.p.=120°–122° C.; 3-isopropoxy-5,6-bis(4-methoxyphenyl)-1,2,4-triazine, m.p.=106°–108° C.; and 3-n-propylthio-5,6-bis(4-methoxyphenyl)-1,2,4-triazine, m.p.=88°–90° C.

The ability of the compounds of this invention according to Formula II above to inhibit collagen-induced platelet aggregation is illustrated by the following test procedure.

Blood samples were obtained from 2 healthy human volunteers, who had not taken any medication for at least 3 days prior, and inparticular, asperin for 7 days, by a clean antecubital vein puncture in the forearm with a 19 gauge thin walled disposable needle and a 30 ml. disposable plastic syringe. Twenty-five and one-half ml. of the native blood was immediately transferred into a 40 ml. siliconized centrifuge tube containing 4.5 ml. of acid-citrate anticoagulant (2.2% sodium citrate+1.2% citric acid in saline), capped with Parafilm ® and mixed gently by inverting 6 times. Platelet rich plasma (PRP) was prepared by centrifugation at 164×G. for 20 minutes. An aliquot of the PRP was centrifuged at 3000×g. for 15 minutes to obtain platelet poor plasma (PPP).

Platelet aggregation in platelet rich plasma was measured by the conventional optical density method using a Payton Aggregometer. The instrument was set to give a standard recorder pen deflection for the difference in optical density between platelet rich and platelet poor plasma. Each compound under test was dissolved in saline, the pH adjusted to 7.4 and then properly diluted with saline for use. The reaction mixture consisted of 0.05 ml. of the compound solution+0.5 ml. of collagen suspension (6.9 mcg/ml.). A stock acid soluble collagen solution was prepared according to the method of Cazenave, et al. (J. Lab. Clin. Med. 82, 978:1973) which upon dilution with saline yielded a collagen suspension. For the platelet aggregation studies a 1:360 dilution of the stock acid soluble collagen with saline was employed.

The washed platelet suspension was prepared according to Method B described by Rosi (J. Lab. Clin. Med. 78, 483:1971) with minor modifications. An aliquot of the PRP was centrifuged at 1020×g. for 15 minutes to obtain a platelet pellet and the supernatant was discarded. The platelets were then washed twice in 1/20 volume of acid-citrate (2.2% sodium citrate plus 1.2% citric acid saline) plus sufficient artificial medium heated to 37° C. to bring the volume to the original PRP volume. The artificial medium was composed of 140 mM NaCl, 5 mM KCl and 5 mM glucose in distilled water. The platelets were resuspended by using a siliconized glass Pasteur pipette and a rubber bulb. After resuspension the platelets were separated from the wash by centrifugation at 650×g. for 10 minutes. After the last wash the platelets were suspended in the artificial medium and the pH adjusted to 7.4 with Tris buffer. Platelet aggregation was measured as described above for platelet rich plasma. For the induction of platelet aggregation with collagen, a saline suspension of collagen, containing 0.6 mg/ml., was employed. The reaction mixture consisted of 0.4 ml. platelet suspension+0.05 ml., 1.8 mM $CaCl_2$+0.05 ml. 4 mg/ml. fibrinogen (KABI, Grade L, human)+0.05 ml. of a solution of the compound under test+0.05 ml. collagen suspension.

The results of the above test are set forth in Table 1. In Table 1, the first four columns give the substituents R, $R^1$, $R^2$ and X in the generalized formula at the head of the table, col. 5, the concentration of the compound under test which inhibited collagen-induced platelet aggregation and col. 6 the collagen dilution employed.

TABLE 1

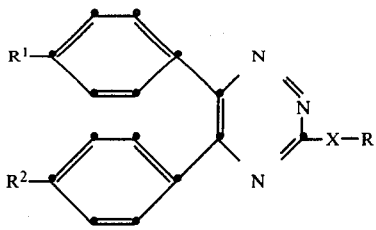

| R | R¹ | R² | X | Inhibitory Concentration mcg./ml. | Collagen dilution |
|---|---|---|---|---|---|
| isopropyl | OCH₃ | OCH₃ | O | 90.1 | 1:360 |
| ethyl | " | " | " | 90.1 | 1:360 |
| methyl | " | " | " | 90.1 | 1:360 |
| methyl | OCH₃ | OCH₃ | — | <0.02 | 1:180 |
| ethyl | " | " | — | 90.1 | 1:180 |
| n-butyl | " | " | — | 90.1 | 1:360 |
| isopropyl | " | " | — | 90.1 | 1:360 |
| methyl | OC₂H₅ | OC₂H₅ | — | 90.1 | 1:360 |
| n-propyl | OCH₃ | OCH₃ | S | 0.13 | 1:45 |
| n-butyl | " | " | " | 90.1 | 1:360 |
| sec-butyl | " | " | " | 0.18 | 1.90 |

The compounds according to Formula II above are employed in my novel anti-thrombotic methods in the form of creams, salves, gels, ointments and the like pharmaceutical formulations customarily employed for topical application. Suitable topical pharmaceutical formulations are given below.

GEL

| | mg/gm |
|---|---|
| Carbopol 940 | 8 |
| Disodium EDTA | 0.2 |
| Polyethylene glycol 400 | 100 |
| Benzyl alcohol | 20 |
| Ethanol 95% | 100 |
| Polysorbate 80 | 100 |
| Sodium hydroxide reagent | 0.8 |
| Purified water to | 1 gm. |

CREAM

| | mg/gm |
|---|---|
| Propylene glycol | 250 |
| Stearic acid | 150 |
| Cetyl alcohol | 50 |
| Mineral oil (heavy) | 40 |
| Polyoxyl 40 stearate | 50 |
| Purified water to | 1 gm |

OINTMENT G

| | mg/gm |
|---|---|
| White petrolatum | 280.0 |
| Mineral oil (heavy) | 150.0 |
| Ceresin | 30.0 |
| Wool wax alcohols | 60.0 |
| Methyl paraben | 0.3 |
| Propyl paraben | 0.1 |
| Water, purified to | 1.0 gm |

HYDROPHILIC OINTMENT

| | gm/100 gm |
|---|---|
| White petrolatum | 14.74 |
| OZOKERITE WAX | 3.16 |
| ARLAAL | 1.88 |
| Beeswax, white | 7.46 |
| Beeswax, synthetic | 4.99 |
| Stearyl alcohol | 0.32 |
| cetyl alcohol | 0.32 |
| anhyd. lanolin | 3.34 |
| Preservatives* | 0.85 |
| Water to | 100. |

*methyl and propyl parabens, sodium tetraborate

In all of the above formulations, the active drug according to Formula II is incorporated in the formulation to give a 5% concentration.

For use in humans one of the above formulations plus a drug from Formula II is applied topically in an amount sufficient to provide 2.5 mcg. per 12 cm² area of skin. Blood levels of 10 nanograms per ml. or higher are readily achievable. In a clinical trial with human volunteers, 5,6-bis-(p-methoxyphenyl)-3-methyl-1,2,4-triazine applied topically gave significant suppression of collagen-induced platelet aggregation in 5 out of 6 subjects.

I claim:

1. A method of achieving an anti-thrombotic effect in mammals which comprises administering topically to a mammal in need of such treatment, an anti-thrombotically-effective amount of a triazine of the formula

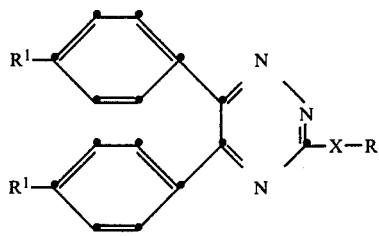

II wherein R is $C_1$–$C_4$ alkyl, X is S, O or a direct bond and each $R^1$ individually is ($C_1$–$C_3$)alkyl-O-.

2. A method of attaining an anti-thrombotically-effective blood-level of a triazine of the formula

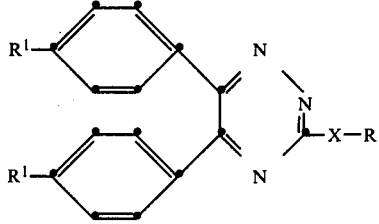

II wherein R is $C_1$–$C_4$ alkyl, X is S, O or a direct bond and each $R^1$ individually is ($C_1$–$C_3$)alkyl-O-, which comprises applying said triazine topically to a mammal in need of antithrombotic treatment.

3. A process according to claims 1 or 2 in which 5,6-bis-(p-methoxyphenyl)-3-methyl-1,2,4-triazine is applied topically.

4. A process according to claims 1 or 2 in which 3-n-propylmercapto-5,6-(p-methoxyphenyl)-1,2,4-triazine is applied topically.

5. A process according to claims 1 or 2 in which 3-n-butylmercapto-5,6-bis-(p-methoxyphenyl)-1,2,4-triazine is applied topically.

6. A process according to claims 1 or 2 in which 3-methoxy-5,6-bis-(p-methoxyphenyl)-1,2,4-triazine is applied topically.

* * * * *